United States Patent [19]

Fedin et al.

[11] Patent Number: 4,992,243
[45] Date of Patent: Feb. 12, 1991

[54] METHOD OF STERILIZING ANTHERS

[76] Inventors: Marat A. Fedin, ulitsa Dm. Ulyanova, 24, kv. 158; Tatyana A. Kuznetsova, Khoroshevskoe shosse, 36b, kv. 62, both of Moscow; Leonid K. Voskoboinik, ulitsa Pushkina, 35, kv. 6, Krasnodar; Tatyana S. Fedorenko, ulitsa Shkolnaya, II, kv. 23, Krasnodar; Alexandra T. Prokopenko, Peredo vaya ulitsa, 74, kv. 24, Krasnodar; Ivan V. Martynov, prospekt Mira, 112, kv. 221, Moscow; Jury P. Belov, ulitsa Tsentralnaya, 4, kv. 85, Moskovskaya oblast, Noginsky raion; Vyacheslav V. Kormachev, ulitsa Elgera, 16, kv. 161; Oleg A. Kolyamshin, ulitsa Dekabristov, 14, korpus 1, kv. 105, both of Cheboxary; Valentin A. Savchuk, opytnaya stantsia VIR, Poltavskaya oblast, Globinsky raion, selo Ustimovka; Leonid S. Shevnitsyn, ulitsa Vinokurova, 7, kv. 31, Novocheboxarsk; Valery V. Smirnov, bulvar Gidrostroitelei, 6, kv. 10, Novocheboxarsk; Viktor A. Gradov, ulitsa Vinokurova, 7, kv. 16, Novocheboxarsk; Sergei I. Paklin, ulitsa Malaya Filevskaya, 66, kv. 30, Moscow; Svetlana A. Novikova, ulitsa Shirokaya, 19, korpus 2, kv. 176, Moscow; Alexandr A. Vishnyakov, ulitsa 2 Parkovaya, 2/16, Moskovskaya oblast, Mytischi; Alexei J. Axinenko, Shkolny bulvar, 1b, kv. 59a, Moskovskaya oblast, Noginsky raion, poselok Chernogolovka; Marina G. Rudakova, ulitsa Flotskaya, 26, kv. 102, Moscow, all of U.S.S.R.

[21] Appl. No.: 442,367
[22] PCT Filed: Mar. 17, 1988
[86] PCT No.: PCT/SU88/00058
 § 371 Date: Jan. 8, 1990
 § 102(e) Date: Jan. 8, 1990
[87] PCT Pub. No.: WO89/08401
 PCT Pub. Date: Sep. 21, 1989

[51] Int. Cl.$^5$ .............................. A01H 1/04
[52] U.S. Cl. .......................... 422/28; 47/58; 47/DIG. 1; 71/65; 71/76; 422/37
[58] Field of Search ............... 47/58, DIG. 2; 71/65, 71/76; 422/28, 37

[56] References Cited

U.S. PATENT DOCUMENTS 4,459,152  7/1984  Fankhauser et al. ........... 47/DIG. 1

FOREIGN PATENT DOCUMENTS 640710   1/1979  U.S.S.R. .
829058   5/1981  U.S.S.R. .
906457   2/1982  U.S.S.R. .
931087   5/1982  U.S.S.R. .
965337  10/1982  U.S.S.R. .
1567153  5/1980  United Kingdom .
2140003 11/1984  United Kingdom .

OTHER PUBLICATIONS

Louis Nickell, "Plant Growth Regulators," Springer Verlag, New York, 1982, pp. 28–31.

Primary Examiner—Robert J. Warden
Assistant Examiner—Timothy M. McMahon
Attorney, Agent, or Firm—Burgess, Ryan & White

[57] ABSTRACT

The present invention relates to the art of agriculture. The method of sterilizing anthers of plants comprises treatment of the plants with a sterilizing agent in combination with a diluent during the period of the fifth and/or sixth stage of organogenesis. According to the invention, as the sterilizing agent use is made of derivatives of phosphoric acids of the general formula:

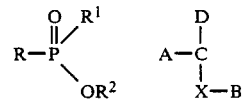

wherein R is H, a $C_1$–$C_4$ alkoxy, dimethylamine, wherein X is O, NH; B is H, a $C_1$–$C_4$ alkyl, phenyl, D is H, $CH_3$; A is a $C_1$–$C_4$ alkyl, phenyl furyl; R' is OH, $ONH_4$, $OAlk(C_1$–$C_4)$, phenyl; $R^2$ is a $C_1$–$C_4$ alkyl, $NaNH_4$, $NH_3Alk(C_1$–$C_4)$, $NH_2Alk_2(C_1$–$C_4)$, or mixtures thereof. The method according to the present invention is useful in selection and seed production.

4 Claims, No Drawings

METHOD OF STERILIZING ANTHERS

FIELD OF THE ART

The present invention relates to the art of biology and agriculture and, more particularly, to a method of sterilization of anthers which is useful in selection and seed production.

PRIOR ART

At present the world is facing the problem of intensification of the agriculture, in particular, of raising yields of grain crops, fodder, vegetable and industrial plants by way of an extensive application of the firstgeneration hybrids. Due to the heterosis phenomenon these hybrids are distinguished from the parental forms by a higher productivity (by 25 to 30%) and by a high quality of the products. Known in the art is a method of breeding novel hybrids based on a "cytoplasmic male sterility-fertility reductants" system. This method is based on a longtime (taking 12-14 years) and complicated selection work involving the creation of sterile analogs, of sterility-fixing agents and fertility reductants. Most promising are methods based on sterilization of anthers by means of chemical sterilizing agents (gametocides). The use of gametocides proves to be much more economically efficient than the use of the "cytoplasmic male sterility" system, since there is no necessity in creating such forms as a sterile analog, an analog of sterility fixation in maternal forms and an analog of fertility reduction in paternal forms. It is practically possible to obtain seeds of first-generation hybrids both in the course of the selection studying of the initial forms and in the organization of their industrial production.

By now about 200 compounds have been found which display a gametocidal activity and belong to the different classes of chemical compounds as regards their chemical structure. Gametocides must cause complete male sterility in the treated plants, while preserving the viability of ovicells and ensuring setting in open pollination at a sufficiently high level (preferably, not less than 70% of the control). Their phytotoxicity and toxicity for the warm-blooded must be minimal.

Known in the art are methods for sterilizing the anthers of cereal crops (L.J.Nickell. Plant Growth Regulators. Application in Agriculture. Moscos, "Kolos" Publishers, 1984, pp. 28-31; SU, A, 906457) which comprise treatment of the plants with sterilizing agents such as 2-chloroethylphosphonic acid (Ethrel), maleic acid hydrazide, di-(polyfluoroalkyl)-phosphoric acid and salts thereof, and the like. The treatment of the plants with sterilizing agents is effected at the V or VI stage of the organigenesis (after F.M.Kuperman).

At the V-th stage of the organogenesis the processes of the formation and differentiation of florets begin. AT the end of this stage neoplasms originate: sporogenous archisporeal tissues. At this stage the initiation of the stamina, pistil and integumentary organis of the floret occurs. At the V-th stage the beginning of differentiation of the stamen primordium into a connective and pistil is observed. The VI-th stage is characterized by the process of the floret formation (micro- and macrosporogenesis). At this stage individual mononuclear pollen grains are usually formed (F.M. Kuperman, "Morphophysiology of Plants", Moscos, "Vysshaya Shkola" Publishers, 1973, pp. 30-36).

Also known in the art is a method of sterilizing the anthers of gramineous plants (GB, A, 1,567,153) which comprises treating the gramineous plants with a sterilizing agent during the period between the appearance of the second internode and earing. As the sterilizing agent heterocyclic compounds are used, the main representatives thereof being 2-carboxy-3, 4-methanopyrrolidine or 2-methoxycarbonyl-3, 4-methanopyrrolidine. These compounds are used in combination with diluents and surfactants.

DISCLOSURE OF THE INVENTION

The present invention is directed to the provision, by selecting appropriate sterilizing agents, of a method enabling its application to sterilization of the anthers of a broad range of crops with a high efficiency of sterilization, while preserving a high settability of seeds in open pollination.

This problem is solved by that in a method for sterilization of the anthers of plants by way of treating them with a sterilizing agent in combination with a diluent during the fifth and/or sixth stage of the organogenesis, in accordance with the present invention as the sterilizing agent use is made of phosphoric acid derivatives of the general formula:

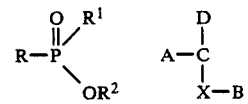

wherein R is H, a $C_1$–$C_4$-alkoxy, dimethylamine,
wherein X is O, MH; B is H, a $C_1$–$C_4$-alkyl, phenyl; D is H, $CH_3$; A is a $C_1$–$C_4$ alkyl, phenyl, furyl; $R^1$ is OH, $ONH_4$, $OAlk(C_1$–$C_4)$, phenyl; $R^2$ is a $C_1$–$C_4$-alkyl, Na, $NH_4$, $NH_3Alk(C_1$–$C_4)$, $NH_2(Alk)_2(C_1$–$C_4)$, or mixtures thereof.

The sterilizing agent can be used in combination with any known acceptable diluent. It is advisable to use it in combinations with water in the form of a 0.1–2% aqueous emulsion or a solution. As the plants to be treated with this sterilizing agent it is preferred to use gramineous plants of sunflower.

The method according to the present invention makes it possible to obtain a male sterility of the plants (98–100%) and to retain a high percentage of settability of seeds (above 70%). In order to ensure a high level of sterilization of the anthers under unfavourable climatic conditions, a repeated treatment of the plants with the sterilizing agent is effected during the periods of the fifth and/or sixth stages of organogenesis (after Kuperman).

PREFERRED EMBODIMENT OF THE INVENTION

The method according to the present invention is carried out in the following manner.

Plants such as winter and spring wheat, diploid and tetraploid rye, triticale, millet, sunflower and the like are treated with a sterilizing agent which represents phosphoric acid derivatives of the general formula:

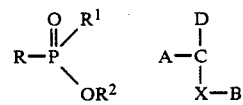

wherein R is H, a $C_1$-$C_4$-alkoxy, dimethylamine,
wherein X is O, NH; B is H, a $C_1$-$C_4$-alkyl, phenyl; D is H, $CH_3$; A=a $C_1$-$C_4$ alkyl, phenyl, furyl, $R^1$ is OH, $ONH_4OAlk(C_1$-$C_4)$, phenyl; $R^2$ is a $C_1$-$C_4$-alkyl. Na, $NH_4$, $NH_3Alk(C_1$-$C_4)$, $AH_2(Alk)_2(C_1$-$C_4)$, of mixtures thereof.

The derivatives of phosphoric acid can be used in combination with any acceptable diluents. It is advisable to use water as the diluent. It is preferable to use a 0.1–2% aqueous emulsion or a solution of the above-mentioned compounds.

When desired, any suitable surfactants can be added to the working solutions. Usually it is advisable to add, to the working solutions upon application thereof onto the plants, any known auxiliary additives such as wetting agents, dispersing agents, adhesives.

The sterilizing agent can be applied to the plants by various methods of treatment such as hydraulic spraying, air spraying (aerosols). The treatment of the plants with the sterilizing agent is carried out during the period of the fifth and/or sixth stage of organigenesis (after Kuperman). The does of the sterilizing agent depends on the nature of the compound, on the crop being treated, on the stage of the treatment and on the natural and climatic factors. In order to ensure a high sterilizing effect under unfavourable coimatic conditions, it is advisable to carry out a repeated treatment of the plants at the VI-th stage of organogenesis. The total dose of the sterilizing agent ranges from 0.6 to 20 kg/ha.

All the derivatives of phosphoric acids employed as the sterilizing agent according to the present invention have been tested for toxicity in experiments on animals. The results of the experiments have shown that these compounds are low-toxic or substantially non-toxic ones.

Thus the compounds according to the present invention such as monosodium phosphite, monomethylammonium phosphite, diammonium phosphite, monoammonium phosphite, methylammonobutyl phosphite, dimethylammoniummonomethyl phosphite, triethylphosphite, dimethylphosphite, diethylphosphite, diisopropylphosphite have the $LD_{50}$=1,000–4,000 mg/kg of the animal's bodymass. All other derivatives of phosphoric acids have their $LD_{50}$ over 1,000 mg/kg.

The derivatives of phosphoric acids are obtained according to conventional procedures such as by way of reacting a corresponding carbonyl compound, an amine and a hyddrophosphoryl component, or by way of reacting alcohols with phosphorus trichloride, or by reacting a corresponding base with acidic components.

The present of gametocidal activity in the sterilizing agents according to the present invention has been revealed in field tests in different soil and climatic zones on 10 $m^2$ plots in 3- and 4-fold tiers. Each sterilizing agent has been tested for at least five years.

The occurrence of the organogenesis stages is controlled cytologically. The treatment of the plants with the sterilizing agent is conducted at the beginning of the fifth stage of the organogenesis after Kuperman.

In the course of earing, the main ears and other tiers are isolated by means of parchment isolators. For wheat and triticale individual isolators are used. For rye one ear from 5 to 7 different adjacents plants is brought under one common isolator. For millet each panicle is isolated individually. The percentage of sterility (X) for wheat, rye, triticale and millet is calculated according to the formula:

$$X = \left[ 1 - \frac{\text{the number of seeds set under the isolator in the treated plants}}{\text{the number of seeds set under the isolator in the control untreated plants}} \right] \times 100\%$$

The number of grains in the non-isolated ears of the control plants is assumed to be a 100% settability in open pollination.

To obtain reliable data, use is made of 20–25 isolators from each tier for wheat and triticale, 10–15 isolators from each tier for rye and millet.

To control the chemical sterilization of sunflower pollen, 45 treated plants on each tier are used for each compound; 15 plants out of them are isolated for open pollination; the heads of other 15 plants are pollinated with a mixture of pollen gathered on 20–25 treated isolated heads and 15 plants are left for open pollination with the view to check the settability of the achenes with the paternal-form pollen.

The male sterility of the plants of sunflower is assessed by the results of fertility and viability of the pollen, morphological features of spermatozoa and setting percentage of the achenes in pollination of the treated plants with the pollen from the non-treated paternal form. The viability of the ovicell is determined from the setting of seeds in the treated plants in open pollination with the paternal form.

The treatment of the plants should be preferably carried out in clear calm weather. All the compounds penetrate into the plant tissues within the period of 4 hours. In the case of rainfall during the 4-hours' period, it is necessary to retreat the plants at the VI-th stage of the organogenesis.

For a better understanding of the present invention the following examples illustrating the embodiments of the method according to the present invention are given hereinbelow.

EXAMPLES 1 to 12.

Plants of winter wheat of Mironovskaya 808 variety are treated at the V-th stage of organogenesis (after Kuperman) by spraying, from a knap-sack sprayer, with a 2% aqueous emulsion of the following sterilizing agents: diethyl-N-methyl-α-aminobenzylphosphonate, diethyl-N-phenyl-α-aminofurylmethyl-phosphonate, dimethyl-N-ethyl-α-aminobenzylphosphonate, dimethyl-N-methyl-2-aminofurylmethylphosphonate, diethyl-α-amino-α-methylpropylphosphonate, diethyl-N-methyl-2-aminofurylmethylphosphonate, diethyl-α-hydroxyfurylmethylphosphonate, diethyl-N,N-dimethylamidophosphate, diethyl-N-methyl-α-aminofurylmethylphosphonate, diethyl-α-aminoethylphosphonate, diethyl-N-ethyl-α-aminofurylmethylphosphonate, diisopropyl-N-methyl-α-aminofurylmethylphosphonate respectively.

As the emulsifying agent added is 0.1% by mass of calcium $C_{12}$-$C_{14}$-alkylbenzenesulphonate. The emulsion also contains, as the adjuvant, 0.01% by mass of dimethylsulphoxide. The rate of consumption of the preparation is 20 kg/ha. Serving as the control are the plants treated with the diluent without the sterilizing agent. The results of the tests are shown in Table I hereinbelow. Similar results are obtained in the treatment of the plants at the VI-th stage of the organogenesis.

TABLE 1

| No. 1 | Example No. 2 | Number of grains in ear under isolator 3 | Sterility percentage 4 | Number of grains in open-pollination 5 | Percentage of setting in open pollination 6 |
|---|---|---|---|---|---|
| 1. | Control | 38.3 | 0.0 | 41.0 | 100.0 |
| 2. | Example 1 | 0.0 | 100.0 | 33.8 | 82.4 |
| 3. | Example 2 | 0.1 | 99.7 | 36.9 | 90.0 |
| 4. | Example 3 | 0.3 | 99.2 | 39.7 | 96.8 |
| 5. | Example 4 | 1.5 | 96.1 | 40.2 | 98.0 |
| 6. | Example 5 | 0.0 | 100.0 | 35.4 | 86.3 |
| 7. | Example 6 | 0.6 | 98.4 | 37.8 | 92.2 |
| 8. | Example 7 | 2.6 | 93.2 | 34.9 | 85.1 |
| 9. | Example 8 | 0.2 | 99.5 | 36.6 | 89.3 |
| 10. | Example 9 | 0.0 | 100.0 | 37.1 | 90.5 |
| 11. | Example 10 | 0.0 | 100.0 | 35.4 | 86.3 |
| 12. | Example 11 | 1.6 | 95.8 | 28.0 | 68.3 |
| 13. | Example 12 | 0.8 | 97.9 | 40.7 | 99.3 |

EXAMPLES 13 to 23

Plants of winter wheat of Priboy variety are treated at the V-th stage of organogenesis (after Kuperman) by spraying a 2% aqueous emulsion of the following sterilizing agents; diethyl-N-methyl-α-aminobenzylphosphonate, diethyl-N-phenyl-α-aminofurylmethylphosphonate, dimethyl-N-ethyl-α-aminobenzylphosphonate, dimethyl-N-methyl-2-aminofurylmethylphosphonate, diethyl-α-amino-α-methylpropylphosphonate, diethyl-N,N-dimethylamidophosphate, diethyl-N-methyl-α-aminofurylmethylphosphonate, diethyl-N-ethyl-α-aminofurylmethylphosphonate, diisopropyl-N-methyl-α-aminofurylmethylphosphonate respectively. As the emulsifying agent, 0.01% by mass of calcium $C_{12}$–$C_{14}$-aklylbenzene-sulphonate is added. The emulsion also incorporates 0.01% by mass of tetrahydrofuran as the adjuvant. The rate of consumption of the preparation is 12 kg/ha. Serving as the control are the plants treated in a manner similar to that described in Example I. The results of the tests are shown in Table 2. Similar results are obtained in the treatment of the plants at the VI-th stage of organogenesis.

TABLE 2

| No. 1 | Example No. 2 | Number of grains in ear under percentage 3 | Sterility percentage, % 4 | Number of grains in ear in open pollination 5 | Percentage of setting in open pollination, % 6 |
|---|---|---|---|---|---|
| 1. | Control | 32.1 | 0.0 | 36.8 | 100.0 |
| 2. | Example 13 | 0.1 | 99.7 | 33.1 | 89.9 |
| 3. | Example 14 | 0.3 | 99.1 | 35.0 | 95.1 |
| 4. | Example 15 | 0.6 | 98.1 | 32.8 | 89.1 |
| 5. | Example 16 | 2.8 | 91.3 | 32.6 | 88.6 |
| 6. | Example 17 | 0.0 | 100.0 | 32.1 | 87.2 |
| 7. | Example 18 | 0.0 | 100.0 | 34.5 | 93.8 |
| 8. | Example 19 | 0.0 | 100.0 | 35.7 | 97.0 |
| 9. | Example 20 | 3.8 | 88.2 | 36.0 | 97.8 |
| 10. | Example 21 | 0.0 | 100.0 | 34.6 | 94.0 |
| 11. | Example 22 | 0.2 | 99.4 | 35.9 | 97.6 |
| 12. | Example 23 | 0.1 | 99.7 | 36.3 | 98.6 |

EXAMPLES 24–29

Plants of winter wheat of Polesskaya-70 variety are treated at the V-th stage of organogenesis (after Kuperman) by way of spraying, from a knap-sack sprayer, with a 2% aqueous emulsion of the following sterilizing agents: diethyl-α-hydroxyfuryl-methylphosphonate, diethyl-N, N-dimethylamidophosphate, diethyl-N-methyl-α-aminofurylmethylphosphonate, diethyl-α-aminoethylphosphonate, diethyl-N-ethyl-α-aminofurylmethylphosphonate, diisopropyl-N-methyl-α-aminofurylmethylphosphonate respectively. As the emulsifying agent 0.1% by mass of calcium $C_{12}$–$C_{14}$-alkylbenzenesulphonate is added.

The emulsion also incorporates, as the adjuvant, 0.01% by mass of dodecylsulphate. The rate of consumption of the preparation is 16 kg/ha. Serving as the control are the plants treated in a manner similar to that described in Example I hereinbefore.

The test results are shown in Table 3 hereinbelow. Similar results are obtained in the treatment of the plants at the VI-th stage of organogenesis.

TABLE 3

| No. 1 | Example No. 2 | Number of grains in ear under isolator 3 | Sterility percentage, % 4 | Number of grains in ear in open pollination 5 | Percentage of grain setting in open pollination, % 6 |
|---|---|---|---|---|---|
| 1. | Control | 38.1 | 0.0 | 34.9 | 100.0 |
| 2. | Example 24 | 3.9 | 83.7 | 30.6 | 87.7 |
| 3. | Example 25 | 0.0 | 100.0 | 33.9 | 97.1 |
| 4. | Example 26 | 0.0 | 100.0 | 31.8 | 91.1 |
| 5. | Example 27 | 0.0 | 100.0 | 32.0 | 91.7 |
| 6. | Example 28 | 0.7 | 97.8 | 30.4 | 87.1 |
| 7. | Example 29 | 0.3 | 99.1 | 33.7 | 96.6 |

EXAMPLES 30–41

Plants of spring wheat of Moskovskaya 35 variety are treated at the VI-th stage of organogenesis (after Kuperman) with a 2% aqueous emulsion of the following sterilizing agents: diethyl-N-methyl-α-aminobenzylphosphonate, diethyl-N-phenyl-α-aminofurylmethylphosphonate, dimethyl-N-ethyl-α-aminobenzylphosphonate, diethyl-N-methyl-α-aminofurylmethylphosphonate, diethyl-N-methyl-α-aminofurylmethylphosphonate, diethyl-α-amino-α-methylpropylphosphonate, dimethylphosphite, diammoniumphosphite, diethyl-N-ethyl-α-aminofurylmethylphosphonate, methylammoniummonobutylphosphite, diethyl-N, N-dimethylamidophosphate, diisopropyl-N-methyl-α-aminofurylmethylphosphonate respectively. As the emulsifying agent, 0.1% by mass of calcium $C_{12}$–$C_{14}$-alkylbenzenesulphonate is added, and as the adjuvant -0.1% by mass of dimethylformamide. The rate of consumption of the preparation is 10 kg/ha. Serving as the control are the plants treated with the diluent without the sterilizing agent. The results of the tests are shown in Table 4. Similar results are obtained in the treatment of the plants at the V-th stage of organigenesis.

TABLE 4

| No. 1 | Example No. 2 | Number of grains in ear under isolator 3 | Sterility percentage, % 4 | Number of grains in ear in open pollination 5 | Percentage of grain setting in open pollination, % 6 |
|---|---|---|---|---|---|
| 1. | Control | 27.5 | 0.0 | 33.2 | 100.0 |
| 2. | Example 30 | 0.0 | 100.0 | 29.8 | 89.8 |
| 3. | Example 31 | 0.1 | 99.4 | 30.1 | 90.7 |
| 4. | Example 32 | 0.6 | 97.8 | 30.6 | 92.2 |
| 5. | Example 33 | 1.3 | 95.2 | 28.8 | 86.7 |
| 6. | Example 34 | 0.1 | 99.4 | 29.1 | 87.6 |
| 7. | Example 35 | 0.1 | 99.4 | 31.5 | 94.9 |
| 8. | Example 36 | 0.0 | 100.0 | 28.4 | 85.5 |
| 9. | Example 37 | 0.4 | 98.5 | 32.3 | 97.3 |
| 10. | Example 38 | 0.0 | 100.0 | 30.7 | 92.5 |

TABLE 4-continued

| No. 1 | Example No. 2 | Number of grains in ear under isolator 3 | Sterility percentage, % 4 | Number of grains in ear in open pollination 5 | Percentage of grain setting in open pollination, % 6 |
|---|---|---|---|---|---|
| 11. | Example 39 | 6.0 | 78.0 | 32.0 | 96.4 |
| 12. | Example 40 | 1.2 | 95.6 | 28.9 | 87.0 |
| 13. | Example 41 | 0.1 | 99.4 | 30.6 | 92.2 |

EXAMPLES 42–47

Plants of spring wheat of Botanicheskaya 4 variety are treated at the VI-th stage of organogenesis (after Kuperman) with a 2% aqueous emulsion of the following sterilizing agents: diethyl-α-hydroxyfurylmethylphosphonate, diethyl-N, N-dimethylamidophosphate, diethyl-N-methyl-α-aminofurylmethylphosphonate, diethylphosphite, diethyl-N-ethyl-α-aminofurylmethylphosphonate, diisopropyl-N-methyl-α-aminofurylmethylphosphonate respectively. As the emulsifying agent 0.1% by mass of calcium $C_{12}$–$C_{14}$-alkylbenzenesulphonate is added, as the adjuvant -0.1% by mass of dimethylsulphoxide. The rate of consumption of the preparation is 8 kg/ha. Serving as the control are the plants treated in a manner similar to that described in Examples 30 to 41. The results of the tests are shown in Table 5. Similar results are obtained in the treatment of the plants at the V-th stage of organogenesis.

TABLE 5

| No. 1 | Example No. 2 | Number of grains in ear under isolator 3 | Sterility percentage, % 4 | Number of grains in ear in open pollination 5 | Percentage of grain setting in open pollination, % 6 |
|---|---|---|---|---|---|
| 1. | Control | 28.2 | 0.0 | 30.1 | 100.0 |
| 2. | Example 42 | 0.0 | 100.0 | 27.8 | 92.4 |
| 3. | Example 43 | 0.1 | 99.7 | 28.1 | 93.4 |
| 4. | Example 44 | 0.0 | 100.0 | 28.8 | 95.7 |
| 5. | Example 45 | 0.3 | 98.9 | 26.5 | 88.0 |
| 6. | Example 46 | 0.0 | 100.0 | 23.6 | 78.1 |
| 7. | Example 47 | 0.1 | 99.7 | 28.4 | 94.4 |

EXAMPLES 48–54

Plants of triticale of PRAG-109 variety are treated at the VI-th stage of organogenesis (after Kuperman) with a 2% aqueous emulsion of the following sterilizing agents: diethyl-N-phenyl-α-aminofurylmethylphosphonate, dimethyl-N-ethyl-α-aminobenzylphosphonate, diethyl-N-methyl-2-aminofurylmethylphosphonate, diethyl-N, N-dimethylamidophosphate, diethyl-α-aminoethylphosphonate, diethyl-N-ethyl-α-aminofurylmethylphosphonate, diisopropyl-N-methyl-α-aminofurylmethylphospohnate respectively. As the emulsifying agent 0.1% by mass of calcium $C_{12}$–$C_{14}$-alkylbenzenesulphonate is added, as the adjuvant - 0.01% by mass of tetrahydrofuran. The rate of consumption of the preparation is 20 kg/ha. Serving as the control are the plants treated in a manner similar to that described in Example I hereinabove. The results of these tests are shown in Table 6 hereinbelow. Similar results are obtained in the treatment of the plants at the V-th stage of organogenesis.

TABLE 6

| No. 1 | Example No. 2 | Number of grains in ear under isolator 3 | Sterility percentage, % 4 | Number of grains in ear in open pollination 5 | Percentage of grain setting in open pollination, % 6 |
|---|---|---|---|---|---|
| 1. | Control | 62.2 | 0.0 | 69.0 | 100.0 |
| 2. | Example 48 | 0.0 | 100.0 | 58.8 | 85.2 |
| 3. | Example 49 | 0.1 | 99.7 | 63.1 | 91.4 |
| 4. | Example 50 | 0.0 | 100.0 | 61.6 | 89.3 |
| 5. | Example 51 | 0.8 | 98.7 | 66.2 | 95.9 |
| 6. | Example 52 | 2.6 | 96.8 | 61.1 | 88.6 |
| 7. | Example 53 | 0.6 | 99.0 | 60.8 | 88.1 |
| 8. | Example 54 | 1.1 | 98.2 | 64.5 | 93.5 |

EXAMPLES 55–57

Plants of triticale of Amphidiploid-206 variety are treated, in a manner similar to that described in Example 60, at the V-th and VI-th stages of organogenesis with a 2% aqueous emulsion of the following sterilizing agents: diethyl-α-aminoethylphosphonate, diethyl-N-ethyl-α-aminofurylmethylphosphonate, diisopropyl-N-methyl-α-aminofurylmethylphosphonate respectively. The rate of consumption of the preparation is 12 kg/ha. The results of the tests are shown in Table 7 hereinbelow.

TABLE 7

| No. 1 | Example No. 2 | Number of grains in ear under isolator 3 | Sterility percentage, % 4 | Number of grains in ear in open pollination 5 | Percentage of grain setting in open pollination, % 6 |
|---|---|---|---|---|---|
| 1. | Control | 31.7 | 0.0 | 36.6 | 100.0 |
| 2. | Example 55 | 0.0 | 100.0 | 30.5 | 83.3 |
| 3. | Example 56 | 0.0 | 100.0 | 33.8 | 92.3 |
| 4. | Example 57 | 0.0 | 100.0 | 32.9 | 89.9 |

EXAMPLES 58–69

Plants of tetrapolid rye of Belta variety are treated in a manner similar to that described in Example I hereinabove with a 2% aqueous emulsion of the following sterilizing agents: diethyl-N-methyl-α-aminobenzylphosphonate, diethyl-N-phenyl-α-aminofurylmethylphosphonate, dimethyl-N-ethyl-α-aminobenzylphosphonate, dimethyl-N-methyl-α-aminofurylmethylphosphonate, diethyl-N-methyl-α-aminofurylmethylphosphonate, diethyl-α-amino-α-methylpropylphosphonate, diisopropylphosphite, diethyl-N, N-dimethylamidophosphate, diethyl-N-methyl-α-aminofurylmethylphosphonate, diethyl-α-aminoethylphosphonate, diethyl-N-ethyl-α-aminofurylmethylphosphonate, diisopropyl-N-methyl-α-aminofurylmethylphosphonate respectively. Serving as the control are the plants treated in a manner similar to that described in Example I hereinabove. The rate of consumption of the preparation is 12 kg/ha. THe results of the tests are shown in Table 8 hereinbelow.

TABLE 8

| No. 1 | Example No. 2 | Number of grains in ear under isolator 3 | Sterility percentage, % 4 | Number of grains in ear in open pollination 5 | Percentage of grain setting in open pollination, % 6 |
|---|---|---|---|---|---|
| 1. | Control | 43.3 | 0.0 | 47.1 | 100.0 |
| 2. | Example 58 | 1.0 | 97.7 | 40.8 | 86.6 |

TABLE 8-continued

| No. 1 | Example No. 2 | Number of grains in ear under isolator 3 | Sterility percentage, % 4 | Number of grains in ear in open pollination 5 | Percentage of grain setting in open pollination, % 6 |
|---|---|---|---|---|---|
| 3. | Example 59 | 0.1 | 99.8 | 42.1 | 89.4 |
| 4. | Example 60 | 0.0 | 100.0 | 36.4 | 77.3 |
| 5. | Example 61 | 0.1 | 99.8 | 43.5 | 92.4 |
| 6. | Example 62 | 0.2 | 99.5 | 44.3 | 94.0 |
| 7. | Example 63 | 0.0 | 100.0 | 45.9 | 97.4 |
| 8. | Example 64 | 3.1 | 92.8 | 42.8 | 90.9 |
| 9. | Example 65 | 0.8 | 98.2 | 45.8 | 97.2 |
| 10. | Example 66 | 2.5 | 94.2 | 32.5 | 69.0 |
| 11. | Example 67 | 0.0 | 100.0 | 44.2 | 93.8 |
| 12. | Example 68 | 0.7 | 98.4 | 37.6 | 79.8 |
| 13. | Example 69 | 0.0 | 100.0 | 42.5 | 90.2 |

EXAMPLES 70-80

Plants of diploid rye of Chulpan variety are treated at the VI-th stage of organogenesis with a 2% aqueous emulsion of the following sterilizing agents: diethyl-N-methyl-α-aminobenzylphosphonate, diethyl-N-phenyl-α-aminofurylmethylphosphonate, dimethyl-N-ethyl-α-aminobenzylphosphonate, dimethyl-N-methyl-α-aminofurylmethylphosphonate, diethyl-N-methyl-α-aminofurylmethylphosphonate, diethyl-α-amino-α-methylpropylphosphonate, diethyl-N, N-dimethylamidophosphate, diethyl-N-methyl-α-aminofurylmethylphosphonate, diethyl-α-aminoethylphosphonate, diethyl-N-ethyl-α-aminofurylmethylphosphonate, diisopropyl-N-methyl-α-aminofurylmethylphosphonate, respectively. As the emulsifying agent 0.1% by mass of calcium alkyl ($C_{12}$–$C_{14}$)-benzenesulphonate and as the adjuvant - 0.01% by mass of dimethylformamide. The rate of consumption of the preparation. Serving as the control are the plants treated in a manner similar to that described in Example I. The results of the tests are shown in Table 9. Similar results are obtained in the treatment of the plants at the V-th stage of organogenesis.

TABLE 9

| No. 1 | Example No. 2 | Number of grains in ear under isolator 3 | Sterility percentage, % 4 | Number of grains in ear in open pollination 5 | Percentage of grain setting in open pollination, % 6 |
|---|---|---|---|---|---|
| 1. | Control | 57.1 | 0.0 | 64.7 | 100.0 |
| 2. | Example 70 | 0.3 | 99.5 | 61.8 | 95.5 |
| 3. | Example 71 | 0.1 | 99.8 | 60.6 | 93.7 |
| 4. | Example 72 | 0.0 | 100.0 | 54.8 | 84.7 |
| 5. | Example 73 | 0.6 | 99.0 | 58.1 | 89.8 |
| 6. | Example 74 | 0.4 | 99.3 | 62.6 | 96.8 |
| 7. | Example 75 | 0.0 | 100.0 | 57.4 | 88.7 |
| 8. | Example 76 | 0.7 | 98.8 | 60.7 | 93.8 |
| 9. | Example 77 | 0.0 | 100.0 | 59.4 | 91.8 |
| 10. | Example 78 | 0.9 | 98.4 | 62.3 | 96.3 |
| 11. | Example 79 | 0.7 | 98.8 | 63.8 | 98.6 |
| 12. | Example 80 | 0.0 | 100.0 | 61.6 | 95.2 |

EXAMPLES 81-92

Plants of diploid rye of Kharkovskaya-55 variety are treated at the VI-th stage of organogenesis with a 2% aqueous emulsion of the following sterilizing agents: diethyl-N-methyl-α-aminobenzylphosphonate, diethyl-N-phenyl-α-aminofurylmethylphosphonate, dimethyl-N-α-ethyl-α-aminobenzylphosphonate, dimethyl-N-methyl-α-aminofurylmethylphosphonate, diethyl-N-methyl-α-aminofurylmethylphosphonate, diethyl-α-amino-α-methylpropylphosphonate, dimethylphosphite, diethyl-N, N-dimethylamidophosphate, diethyl-N-methyl-α-aminofurylmethylphosphonate, diethyl-α-aminoethylphosphonate, diethyl-N-ethyl-α-aminofurylmethylphosphonate, diisopropyl-N-methyl-α-aminofurylmethylphosphonate respectively. As the emulsifying agent 0.1% by mass of calcium $C_{12}$–$C_{14}$-alkylphosphonate is added, as the adjuvant - 0.01% by mass of dodecylsulphate. The rate of consumption of the preparation is 12 kg/ha. Serving as the control are the plants treated in a manner similar to that described in Example I hereinbefore. The results of the tests are shown in Table 10 hereinbelow. Similar results are obtained in the treatment of the plants at the V-th stage of organogenesis.

TABLE 10

| No. | Example No. | Number of grains in ear under isolator | Sterility percentage, % | Number of grains in ear in open pollination | Percentage of grain setting in open pollination, % |
|---|---|---|---|---|---|
| 1. | Control | 38.4 | 0.0 | 46.8 | 100.0 |
| 2. | Example 81 | 0.0 | 100.0 | 40.6 | 86.8 |
| 3. | Example 82 | 0.2 | 99.5 | 42.5 | 90.8 |
| 4. | Example 83 | 0.0 | 100.0 | 39.8 | 85.0 |
| 5. | Example 84 | 0.7 | 98.2 | 44.1 | 94.2 |
| 6. | Example 85 | 0.0 | 100.0 | 32.6 | 69.6 |
| 7. | Example 86 | 0.1 | 99.7 | 43.7 | 93.4 |
| 8. | Example 87 | 0.0 | 100.0 | 40.4 | 86.3 |
| 9. | Example 88 | 0.6 | 98.4 | 44.3 | 94.7 |
| 10. | Example 89 | 0.7 | 98.2 | 40.8 | 87.2 |
| 11. | Example 90 | 0.0 | 100.0 | 44.9 | 95.9 |
| 12. | Example 91 | 0.2 | 99.5 | 40.2 | 85.9 |
| 13. | Example 92 | 0.0 | 100.0 | 39.5 | 84.4 |

EXAMPLES 93-102

Plants of millet of Mironovskoye 94 variety are treated in a manner similar to that of Example 14 with a 1% aqueous emulsion of the following sterilizing agents: diethyl-N-phenyl-α-aminofurylmethylphosphonate, dimethyl-N-methyl-α-aminobenzylphosphonate, dimethyl-N-methyl-α-aminofurylphosphonate, diethyl-N-methyl-α-aminofurylmethylphosphonate, diethyl-α-amino-α-methylpropylphosphonate, diethyl-N, N-dimethylamidophosphate, diethyl-N-methyl-α-aminofurylmethylphosphonate, diethyl-α-aminoethylphosphonate, diethyl-Methyl-α-aminofurylmethylphosphonate, diisopropyl-N-methyl-α-aminofurylmethylphosphonate respectively. The rate of consumption of the preparation is 6 kg/ha. The results are shown in Table II.

TABLE 11

| No. | Example No. | Number of grains in panicle under isolator | Sterility percentage, % | Number of grains in panicle in open pollination | Percentage of setting in open pollination, % |
|---|---|---|---|---|---|
| 1 | Control | 320.5 | 0.0 | 379.5 | 100 |
| 2. | Example 93 | 0.0 | 100.0 | 315.6 | 83.2 |
| 3. | Example 94 | 0.0 | 100.0 | 294.8 | 77.7 |
| 4. | Example 95 | 0.0 | 100.0 | 326.4 | 86.0 |
| 5. | Example 96 | 0.0 | 100.0 | 301.5 | 79.4 |
| 6. | Example 97 | 0.0 | 100.0 | 359.2 | 94.6 |
| 7. | Example 98 | 0.0 | 100.0 | 300.7 | 79.2 |

TABLE 11-continued

| Example No. | Example No. | Number of grains in panicle under isolator | Sterility percentage, % | Number of grains in panicle in open pollination | Percentage of setting in open pollination, % |
|---|---|---|---|---|---|
| 8. | Example 99 | 0.0 | 100.0 | 348.6 | 91.8 |
| 9. | Example 100 | 0.0 | 100.0 | 284.3 | 74.9 |
| 10. | Example 101 | 0.0 | 100.0 | 352.5 | 92.9 |
| 11. | Example 102 | 0.0 | 100.0 | 362.9 | 95.6 |

EXAMPLES 103-111

Plants of millet of Kormovoye-I variety are treated in a manner similar to that described in Example I hereinabove with a 1% aqueous emulsion of the following sterilizing agents: diethyl-N-phenyl-α-aminofurylmethylphosphonate, diethylphosphite, diisopropylphosphite, dimethylammoniummonomethylphosphite, diethyl-α-hydroxyfurylmethylphosphonate, diethyl-N, N-dimethylamidophosphate, diethyl-α-aminoethylphosphonate, diethyl-N-ethyl-2-aminofurylmethylphosphonate, diisopropyl-N-methyl-α-aminofurylmethylphosphonate respectively. The rate of consumption of the preparation is 6 kg/ha. The results of the tests are shown in Table 12 hereinbelow.

TABLE 12

| No. | Example No. | Number of grains in panicle under isolator | Sterility percentage, % | Number of grains in panicle in open pollination | Percentage of setting in open pollination |
|---|---|---|---|---|---|
| 1. | Control | 125.0 | 0.0 | 146.7 | 100.0 |
| 2. | Example 103 | 0.0 | 100.0 | 125.6 | 85.6 |
| 3. | Example 104 | 0.0 | 100.0 | 138.9 | 94.7 |
| 4. | Example 105 | 0.0 | 100.0 | 120.2 | 81.9 |
| 5. | Example 106 | 0.0 | 100.0 | 118.6 | 80.8 |
| 6. | Example 107 | 0.0 | 100.0 | 134.7 | 91.8 |
| 7. | Example 108 | 0.0 | 100.0 | 112.4 | 76.6 |
| 8. | Example 109 | 0.0 | 100.0 | 131.8 | 89.8 |
| 9. | Example 110 | 0.0 | 100.0 | 127.7 | 87.0 |
| 10. | Example 111 | 0.0 | 100.0 | 135.4 | 92.3 |

EXAMPLES 112-118

Plants of sunflower of Peredovik variety, VNIIMK 8931 variety and BK-119 line are treated in a manner similar to that described in Example I hereinbefore with a 1% aqueous emulsion of the following sterilizing agents: diethyl-α-aminoethylphosphonate, diethyl-N-ethyl-α-aminofurylmethylphosphonate, diisopropyl-N-methyl-α-aminofurylmethylphosphonate, diethyl-α-aminoethylphosphonate, diethyl-N, N-dimethylamidophosphate, diethyl-α-aminoethylphosphonate, diethyl-N-phenyl-α-aminofuryl-αmethylphosphonate respectively. The rate of consumption of the preparation is 6 kg/ha. The test results are shown in Table 13.

TABLE 13

| No. | Example No. | Sterility percentage, % | Setting of achenes in open pollination, % | Mass of 1,000 achenes, g | Oil-content of achenes, % | Energy of growth % |
|---|---|---|---|---|---|---|
| | | Sunflower of Peredovik variety | | | | |
| 1. | Control | 0.2 | 85.0 | 84.0 | 54.7 | 100 |
| 2. | Example 112 | 100 | 84.2 | 84.3 | 52.2 | 100 |
| 3. | Example 113 | 100 | 83.3 | 110.0 | 54.9 | 100 |
| 4. | Example 114 | 100 | 81.8 | 83.4 | 52.8 | 100 |
| | | Sunflower of VNIIMK 8931 variety | | | | |
| 5. | Control | 0.5 | 85.7 | 83.0 | 54.7 | 100 |
| 6. | Example 115 | 100 | 84.2 | 83.7 | 55.1 | 100 |
| 7. | Example 116 | 100 | 83.6 | 84.2 | 54.0 | 100 |
| | | Sunflower of BK-119 line | | | | |
| 8. | Control | 2.0 | 85.0 | 60.0 | 51.0 | 100 |
| 9. | Example 117 | 100 | 82.3 | 58.6 | 52.8 | 100 |
| 10. | Example 118 | 100 | 83.8 | 61.4 | 51.6 | 100 |

EXAMPLES 119-122

Plants of winter wheat Mironovskaya 808 variety are treated at the V-th stage of organogenesis with a 2% aqueous emulsion of the following mixtures of sterilizing agents (employed in the ratio I:I): diisopropyl-N-methyl-α-aminofurylmethylphosphonate and dimethylphosphite, diethyl-N-methyl-α-aminofurylmethylphosphonate and diethyl-α-aminoethylphosphonate, diethyl-N, N-dimethylamidophosphate and methylammoniummonobutylphosphite, diethyl-N-phenyl-α-aminofurylmethylphosphonate and diethylphosphate respectively. As the emulsifying agent 0.1% by mass of calcium $C_{12}$-$C_{14}$-alkylbenzenesulphonate is added, as the adjuvant - 0.01% by mass of dodecylsulphate. The rate of consumption of the preparation is 12 kg/ha. Serving as the control are the plants treated in a manner similar to that described in Example I. The results of the tests are shown in Table 14 hereinbelow. Similar results are obtained in the treatment of the plants at the VI-th stage of organogenesis.

TABLE 14

| No. | Example No. | Number of grains in ear under isolator | Percentage of sterility, % | Number of grains in ear in open pollination | Percentage of grain setting in open pollination, % |
|---|---|---|---|---|---|
| 1. | Control | 38.3 | 0.0 | 41.0 | 100.0 |
| 2. | Example 119 | 0.0 | 100 | 39.2 | 95.6 |
| 3. | Example 120 | 0.0 | 100 | 38.6 | 94.1 |
| 4. | Example 121 | 0.0 | 100 | 40.8 | 99.5 |
| 5. | Example 122 | 0.0 | 100 | 39.7 | 96.8 |

EXAMPLES 123-124

Plants of spring wheat of Moskovskaya 35 variety are treated at the V-th stage of organogenesis with a 1% aqueous emulsion of the following mixtures of sterilizing agents (employed in the ratio I:I): diethyl-N-ethyl-α-aminofurylmethylphosphonate and diethyl-N-methyl-α-aminofurylmethylphosphonate; dimethyl-N-methyl-α-aminofurylmethylphosphonate and dimethylphosphite respectively. As the emulsifying agent 0.1% by mass of calcium $C_{12}$-$C_{14}$ -alkylbenzene sulphonate is added, as the adjuvant - 0.01% by mass of dimethylsulphoxide. Serving as the control are the plants treated in a manner similar to that described in Example I hereinbefore. The rate of consumption of the preparation is 6 kg/ha. The results of the tests are shown in Table 15.

Similar results are obtained in the treatment of plants at the VI-th stage of organogenesis.

TABLE 15

| Example No. | Number of grains in ear under isolator | Sterility percentage, % | Number of grains in ear in open pollination | Percentage of grain setting in open pollination, % |
|---|---|---|---|---|
| 1. Control | 27.5 | 0.0 | 33.2 | 100 |
| 2. Example 123 | 0.0 | 100 | 30.6 | 92.2 |
| 3. Example 124 | 0.0 | 100 | 31.8 | 95.8 |

EXAMPLES 125–128

Plants of triticale of PRAG - 109 variety are treated at the V-th stage of organogenesis with a 2% aqueous emulsion of the following mixtures of sterilizing agents (employed in the ratio 1:1): diethyl-N-phenyl-α aminofurylmethylphosphonate and diethylphosphite, diethyl-N-methyl-α-aminobenzenephosphonate and diethyl-α-aminoethylphosphonate, diethyl-N, N-dimethylamidophosphate and dimethylphosphite, diammoniumphosphite and diethyl-N-methyl-α-aminofurylmethylphosphonate respectively. As the emulsifying agent 0.1% by mass of calcium $C_{12}$–$C_{14}$-alkylbenzenesulphonate is added, as the adjuvant 0.01% by mass of tetrahydrofuran. The rate of consumption of the preparation is 12 kg/ha. Serving as the control are the plants treated ion a manner similar to that described in Example I hereinbefore. The test results are shown in Table 16 hereinbelow. Similar results are obtained in the treatment of the plants at the VI-th stage of organogenesis.

TABLE 16

| Example No. | Number of grains in ear under isolator | Sterility percentage, % | Number of grains in ear in open pollination | Percentage of grain setting in open pollination, % |
|---|---|---|---|---|
| 1. Control | 62.2 | 0.0 | 69.0 | 100 |
| 2. Example 125 | 0.0 | 100 | 63.4 | 92.0 |
| 3. Example 126 | 0.0 | 100 | 60.1 | 87.1 |
| 4. Example 127 | 0.0 | 100 | 59.8 | 86.7 |
| 5. Example 128 | 0.0 | 100 | 62.2 | 90.1 |

INDUSTRIAL APPLICABILITY

The method according to the present invention is useful in selection and seed production of highly productive grades and hydrides of crops.

We claim:

1. A method of sterilizing anthers of plants by way of treatment thereof with a sterilizing agent in combination with a diluent during the period of the fifth and/or sixth stage of organogenesis, comprising to said anthers a sterilizing agent made of derivatives of phosphoric acids or mixtures thereof of the general formula:

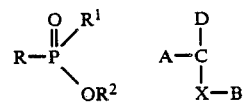

wherein R is H, a $C_1$–$C_4$-alkoxy, dimethylamine,
wherein X is O, NH; B is H, a $C_1$–$C_4$-alkyl, phenyl; D is H, CH$_3$; A is a $C_1$–$C_4$-alkyl, phenyl, furyl; $R^1$ is OH, ONH$_4$, OAlk($C_1$–$C_4$), phenyl; $R^2$ is a $C_1$–$C_4$-alkyl; NaNH$_4$, NH$_3$Alk($C_1$–$C_4$), NH$_2$Alk$_2$($C_1$–$C_4$).

2. A method according to claim 1 wherein said derivatives of phosphoric acids are used in combination with a diluent.

3. A method according to either claims 1–2, wherein the plants to be treated with said sterilizing agent are graminous plants or sunflower plants.

4. A method according to either claims 1 or 2, wherein at least one further application of the sterilizing agent is applied during the periods of the fifth and/or sixth stage of organogenesis to ensure a high level of sterilization of said anthers.

* * * * *